(12) United States Patent
Ferko et al.

(10) Patent No.: US 8,636,800 B2
(45) Date of Patent: Jan. 28, 2014

(54) SOFT TISSUE ATTACHMENT MECHANISM

(75) Inventors: Michael C. Ferko, Warwick, NY (US); Mohamed Soliman, Englewood, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 0 days.

(21) Appl. No.: 13/448,759

(22) Filed: Apr. 17, 2012

(65) Prior Publication Data

US 2012/0203354 A1 Aug. 9, 2012

Related U.S. Application Data

(60) Division of application No. 12/644,297, filed on Dec. 22, 2009, now Pat. No. 8,182,542, which is a continuation-in-part of application No. 12/551,692, filed on Sep. 1, 2009, now Pat. No. 8,226,725.

(51) Int. Cl.
*A61F 2/28* (2006.01)

(52) U.S. Cl.
USPC ..................... 623/16.11; 623/19.11

(58) Field of Classification Search
CPC ..................... A61F 2/28; A61F 2/40
USPC ....... 623/11.11, 16.11, 19.11–19.14
See application file for complete search history.

(56) References Cited

U.S. PATENT DOCUMENTS

| | | | |
|---|---|---|---|
| 3,803,641 A | 4/1974 | Golyakhovsky |
| 3,979,778 A | 9/1976 | Stroot |
| 3,988,783 A | 11/1976 | Treace |
| 4,045,826 A | 9/1977 | Stroot |
| 4,246,660 A | 1/1981 | Wevers et al. |
| 4,355,427 A | 10/1982 | Schneider |
| 4,714,475 A | 12/1987 | Grundei et al. |
| 4,790,850 A | 12/1988 | Dunn et al. |
| 4,790,854 A | 12/1988 | Harder et al. |
| 5,171,322 A | 12/1992 | Kenny |
| 5,330,531 A | 7/1994 | Capanna et al. |
| 6,200,350 B1 | 3/2001 | Masini |
| 6,267,785 B1 | 7/2001 | Masini |

(Continued)

FOREIGN PATENT DOCUMENTS

| | | |
|---|---|---|
| GB | 2126095 A | 3/1984 |
| GB | 2253566 A | 9/1992 |
| WO | 9103993 A1 | 4/1991 |

OTHER PUBLICATIONS

International Search Report, PCT/US2010/047499, Dated Feb. 18, 2011.

(Continued)

*Primary Examiner* — Jason-Dennis Stewart
(74) *Attorney, Agent, or Firm* — Lerner, David, Littenberg, Krumholz & Mentlik, LLP

(57) ABSTRACT

A prosthesis humeral implant has a stem including a coupling element at a proximal end thereof and a head having a coupling element at a distal portion thereof for coupling to the stem portion coupling element. The head has a bearing surface portion for articulating on a prosthetic glenoid and a base portion. A soft tissue attachment element has an L-shape with a mounting flange portion of the L-shape extending and clamped between the bearing portion and base portion. The soft tissue attachment portion has a portion extending proximally from the mounting flange portion. The soft tissue attachment element mounting portion is captured between the head bearing portion and base portion preferably by clamping or being permanently attached to one of the base or bearing portions during manufacture.

19 Claims, 30 Drawing Sheets

(56) References Cited

U.S. PATENT DOCUMENTS

| | | |
|---|---|---|
| 6,267,788 B1 | 7/2001 | Andersson |
| 6,334,874 B1 | 1/2002 | Tornier et al. |
| 6,371,985 B1 | 4/2002 | Goldberg |
| 6,379,391 B1 | 4/2002 | Masini |
| 6,383,225 B2 | 5/2002 | Masini |
| 6,398,812 B1 | 6/2002 | Masini |
| 6,558,425 B2 | 5/2003 | Rockwood, Jr. |
| 6,592,622 B1 | 7/2003 | Ferguson |
| 6,821,300 B2 | 11/2004 | Masini |
| 7,001,429 B2 | 2/2006 | Ferguson |
| 7,070,622 B1 | 7/2006 | Brown et al. |
| 7,175,664 B1 | 2/2007 | Lakin |
| 7,229,478 B2 | 6/2007 | Masini |
| 2003/0216809 A1 | 11/2003 | Ferguson |
| 2004/0002765 A1 | 1/2004 | Maroney et al. |
| 2007/0078516 A1 | 4/2007 | Emami |
| 2007/0173945 A1 | 7/2007 | Wiley et al. |
| 2008/0021554 A1 | 1/2008 | Stone et al. |
| 2008/0234829 A1 | 9/2008 | Mutchler et al. |
| 2011/0130840 A1 | 6/2011 | Oskouei |

OTHER PUBLICATIONS

Maiawer et al., "Proximal Humerus Resection, The Tikhoff-Linberg Procedure and its Modifications", 33 pages (1984).

Stryker, "MRS Upper Extremity: Surgical Protocol", 40 pages, (1988).

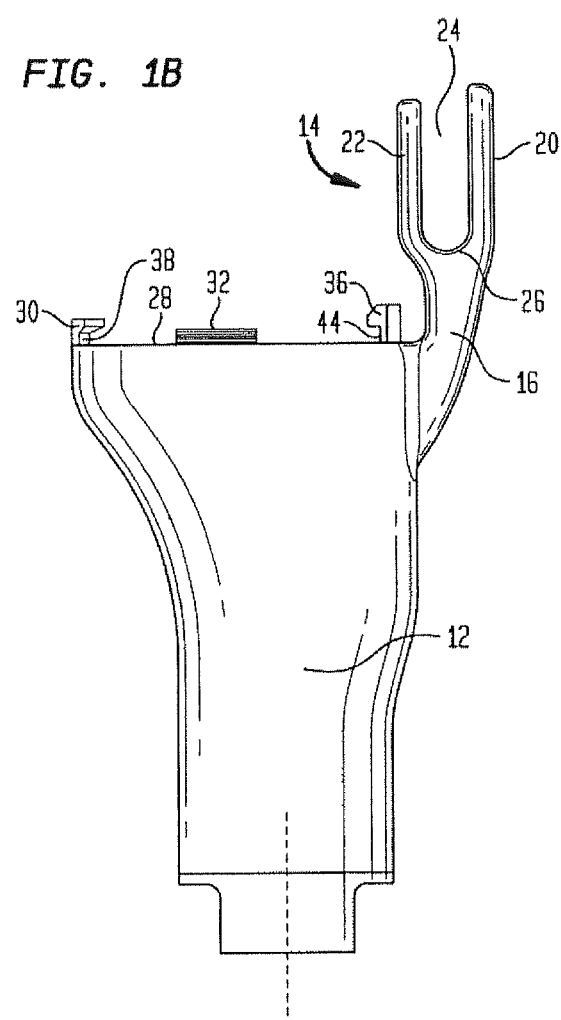

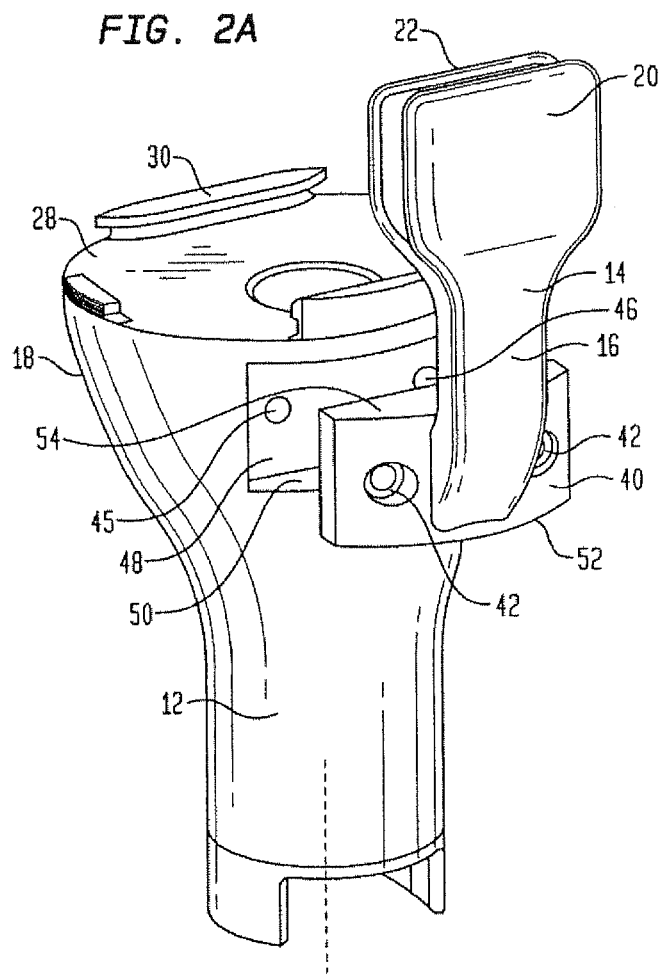

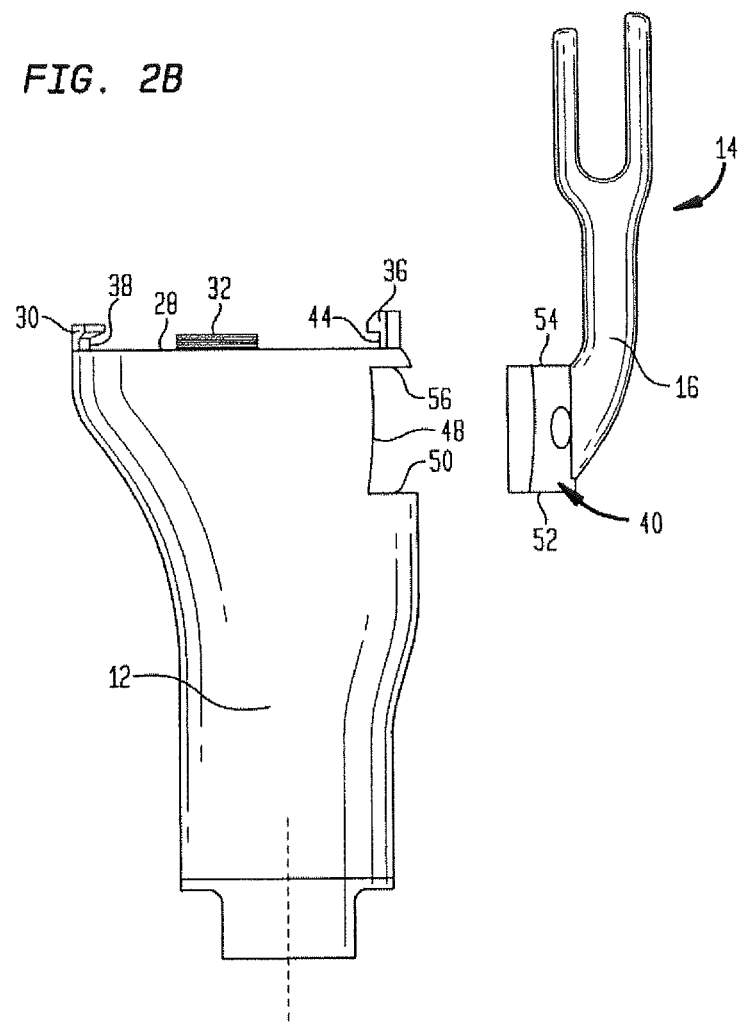

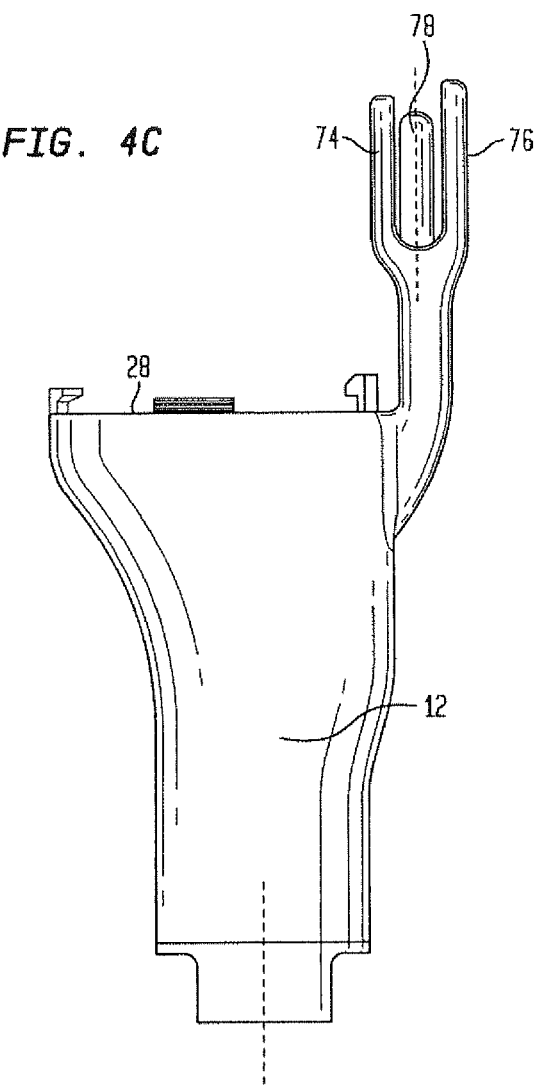

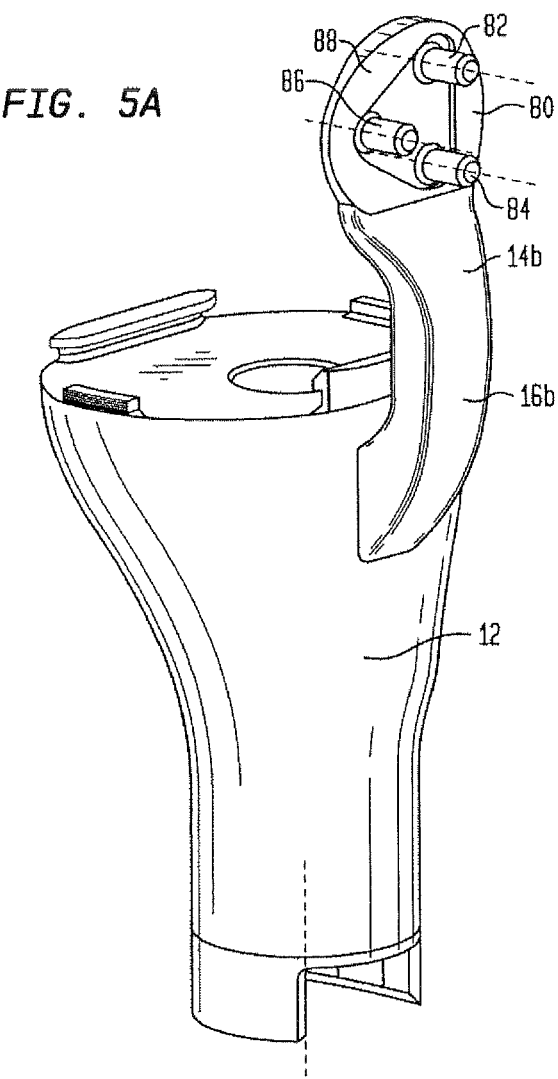

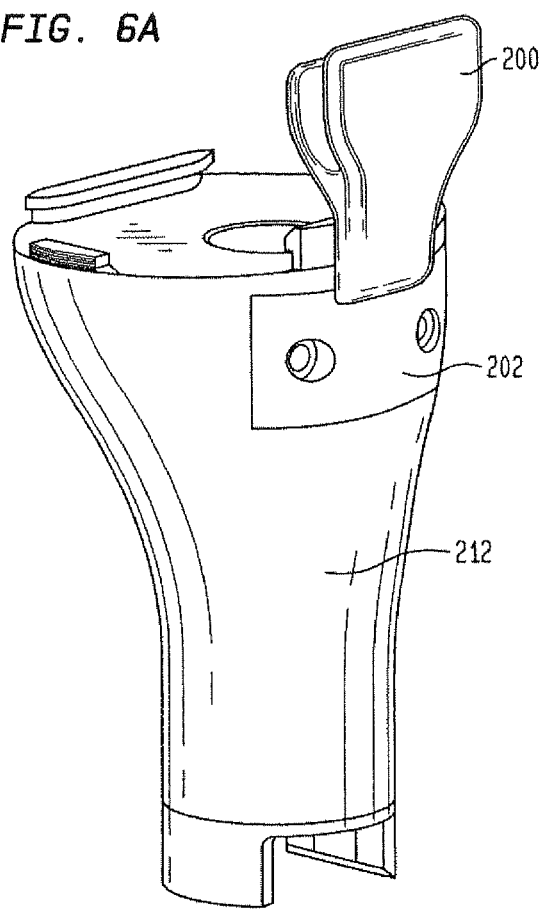

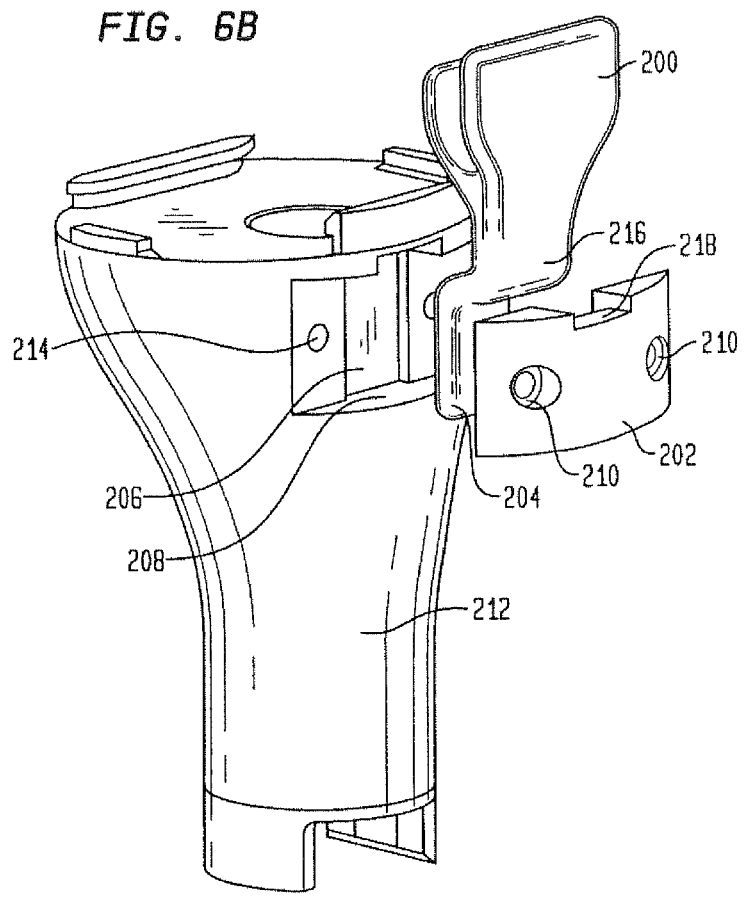

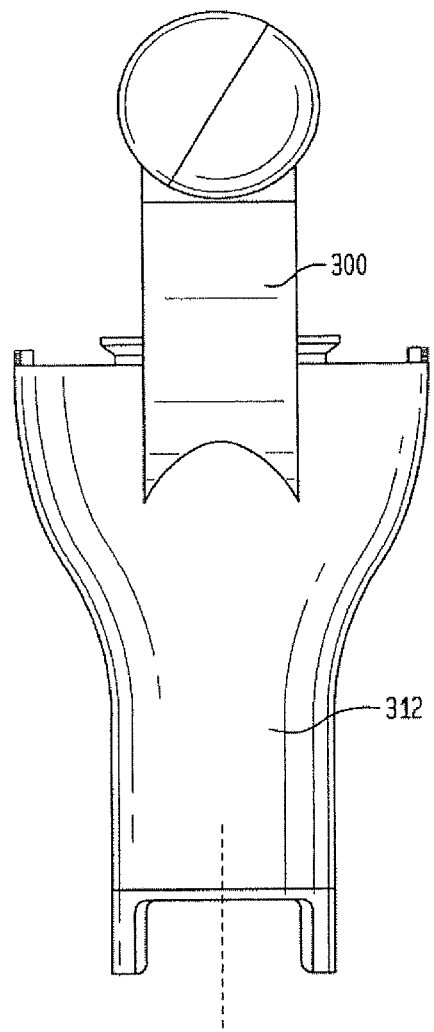

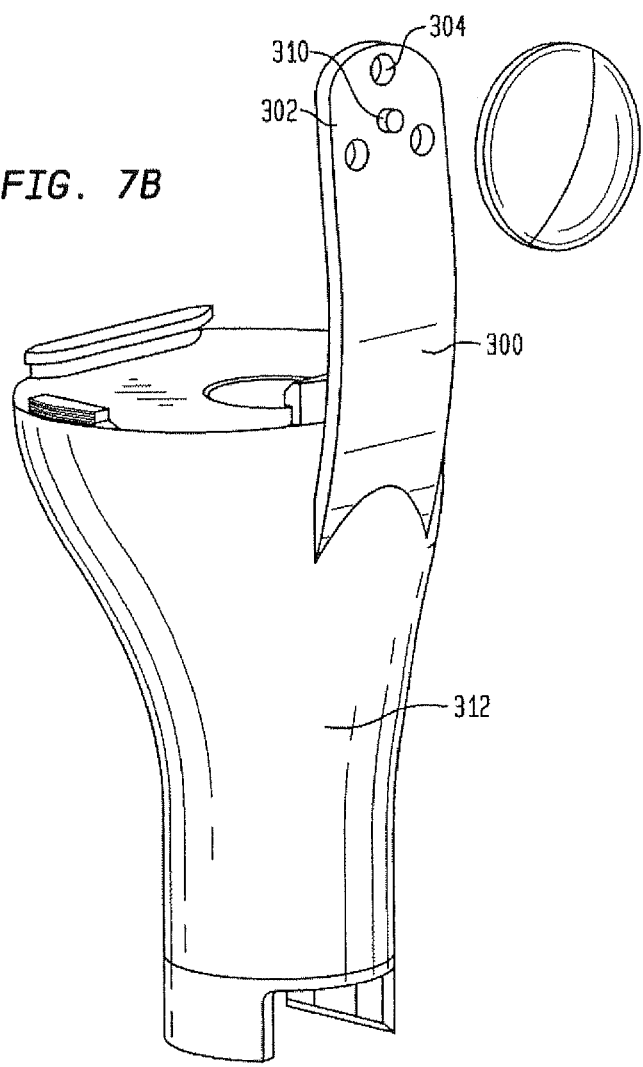

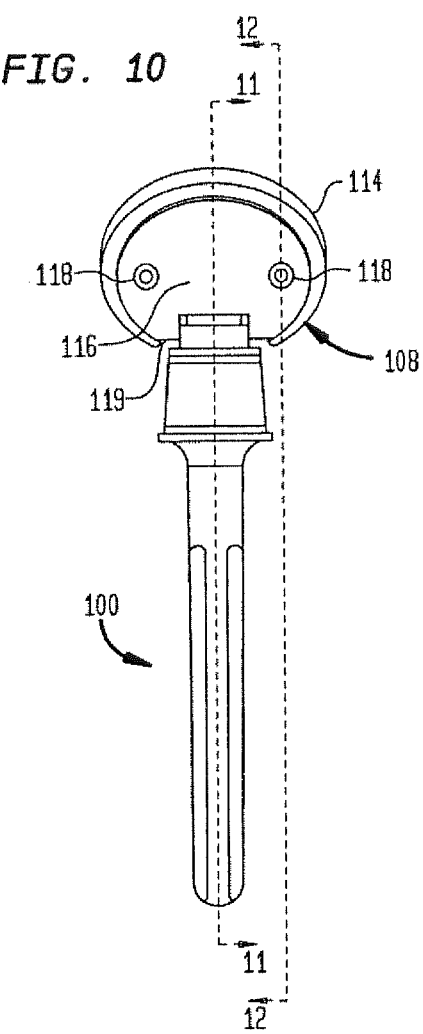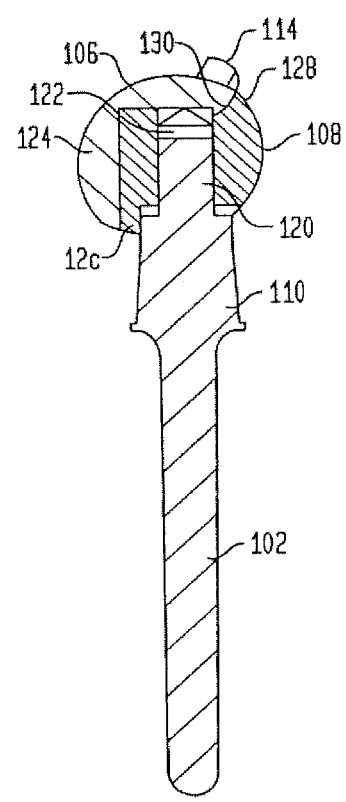

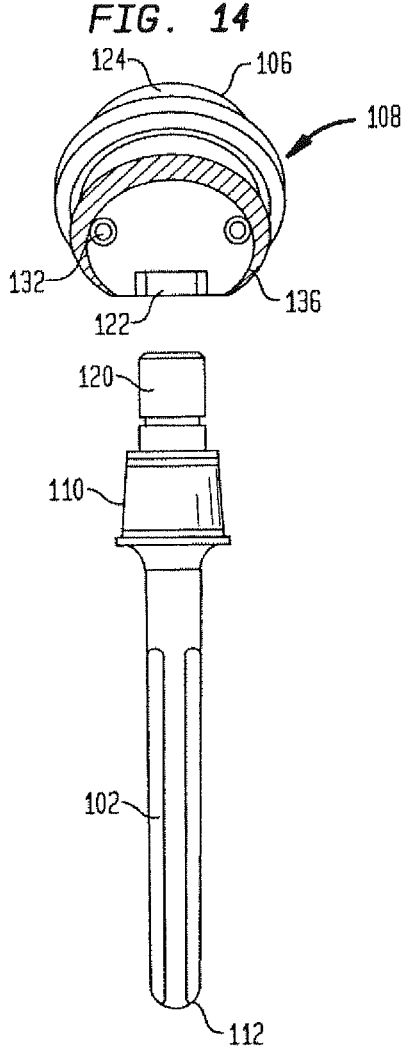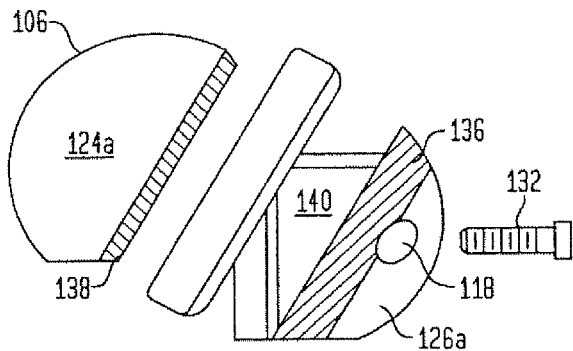

SOFT TISSUE ATTACHMENT MECHANISM

CROSS REFERENCE TO RELATED APPLICATIONS

This application is a divisional of U.S. application Ser. No. 12/644,297, filed on Dec. 22, 2009, which is a continuation-in-part of U.S. application Ser. No. 12/551,692, filed on Sep. 1, 2009, the disclosures of which are incorporated herein by reference.

BACKGROUND OF THE INVENTION

Certain surgical procedures such as oncology surgery and major revision surgery require the resection of the proximal humerus where critical soft tissues (i.e. rotator cuff) attach to the bone. It is typical in these surgeries to bring previously detached tendons to the implant and suture them to the prosthesis. Soft tissue attachment is critical to maintaining movement about the joint and preserving joint stability. It has been difficult to obtain secure attachment of these soft tissues to prostheses for multiple reasons.

First, in natural attachment to bone, there is a transition region of soft tissue to bone (i.e. muscle-tendon-bone) that changes gradually from flexible to rigid. In the reattachment of soft tissue to prosthesis, this transition region is often lost and failure often occurs due to the abrupt change from soft tissue to very rigid metal implants.

Second, in certain procedures resection of surrounding soft tissues along with bony resections are required (i.e. resection to obtain adequate surgical margins during the removal of bone cancer such as osteosarcoma or where bone loss is significant from multiple revision surgeries). This soft tissue resection often leaves the remaining soft tissues too short to reach their original attachment sites, even if adequate methods of attachment directly to metal were available.

Currently, several methods are used to create a functional bridge between soft tissue and prostheses. These methods have exhibited limited success. Where there exists enough length for the soft tissue to reach the prosthesis, the soft tissue is often sutured directly to the prosthesis. Advances have been made in the material and surface treatment of the attachment sites (i.e., the use of porous or foam metals) to improve and promote the in-growth of soft tissue after surgery. However, the relative stiffness of these attachment sites compared to the soft tissue being attached continues to be a limiting factor in the end strength of the tissue/implant interface.

In some joints, when soft tissue length is not adequate to reach the natural attachment site on the prosthesis, graft is sometimes used to create a bridge. Autograft (via transplant or flap) can help to provide additional functional length of the soft tissue, but does not address the stiffness issue. Also, function of the graft host site is also reduced. Furthermore, in the proximal humerus, there are not significant neighboring structures to create substantial tissue flaps for coverage and augmentation of tissue length. Allograft is also an option, however again stiffness is not addressed and known issues of rejection and/or lack of integration with the graft tissue exist. Synthetic materials such as aorta-graft have been used to create a sleeve or bridge between the prosthesis and bone. This can address the stiffness issue at the attachment soft tissue attachment site, however the lack of direct integration of the synthetic material with the prosthesis means that long term loads must be borne by sutures or other attachment mechanisms. As a result, failure of the interface may merely move from the muscle/graft interface to the graft/prosthesis interface.

Typical soft tissue attachment to a humeral prosthesis are shown in U.S. Pat. Nos. 3,803,641, 5,330,531 and 6,398,812 as well as U.S. Patent Application Publication No. 2007/0078516.

In all of the above cases, the preparation and attachment of all of these grafts requires significant time and effort during the surgical setting, which exposes the patient to additional operating room (OR) time in what may be an already lengthy surgical procedure.

BRIEF SUMMARY OF THE INVENTION

One aspect of the humeral head to soft tissue attachment mechanism of the present invention creates a prosthesis that includes an attachment site that is less rigid than the prosthesis itself to provide a more natural transition region for attachment. Additionally, by extending from the prosthesis at or near the natural soft tissue attachment site, the mechanism provides the additional length needed in the event that a portion of the soft tissue needed to be resected as well. In the humerus, this site is distal of the humeral head. It is envisioned that the prosthesis and attachment mechanism could either be monolithic or be modular, providing surgical options if needed.

In another aspect, in a monolithic structure, the attachment material could be compression molded or selectively laser melted into the metal humeral head or any suitable manufacturing means.

It is yet an additional aspect that, in a modular structure, the attachment material could be placed between a two piece humeral head which pieces are subsequently attached together. These could be attached rigidly during manufacturing and sold as one piece or sold separately intended to be attached at the time of surgery.

Although not shown explicitly, it is intended that the attachment mechanism could be provided to the surgeon in an intentionally long length so that the surgeon could trim and shape the protrusion to obtain an optimized attachment site for both size and soft tissue tension.

In one aspect of the invention the attachment mechanism could either be synthetic, biologic, synthetic/biologic composite or hybrid material. The choice of material for attachment would be largely dictated by the requirements of the particular soft tissue being addressed from the perspective of in-growth potential, natural loading requirements, healing potential and other factors.

The material (whether synthetic or biologic) could benefit (depending on site) from being biodegradable or bioresorbable such that over time, it is replaced by the natural soft tissue. In this way, the soft tissue healing would have the opportunity to create a natural soft-to-hard transition region with the prosthesis.

It is also considered that the material (whether synthetic or biologic) could benefit (depending on site) from being porous, especially at the site of soft tissue attachment to promote in-growth. It is also envisioned that technologies could be applied to vary the porosity throughout the attachment mechanism throughout its length (to create varying material properties which would create a more natural transition region) or throughout its cross section (to limit the in-growth of unwanted tissues).

Some examples of suitable synthetic materials are Dacron, polytetra fluorethylene (PTFE), Leeds-Keio (L-K) artificial ligament, Texturized or Open-weave poly(ethylene terephthalate), waterswolen poly(2-hydroxyethyl methacrylate), polydioxanone (PDO), PDO/Elastin Weave), polyurethane (PU), aromatic porous polyurethane, poly-(L-lactic acid)

(PLLA), and Polyetheratherketone (PEEK). Some examples of biologic or hybrid composite materials could be allograft or xenograft tendon or ligament, small-intestinal submucosa (SIS), collagen, cell seeded collagen matrices, hydrogels, Chitosan or other known cell scaffold materials.

A further aspect of the invention provides a method of securing soft tissue to a prosthetic bone implant. The method may comprise implanting a joint bone prosthesis adjacent to a joint at or near a natural soft tissue attachment site, the prosthesis connected to a one-piece soft tissue attachment component. The method may also include suturing the soft tissue attachment component to the natural soft tissue with filaments.

In one embodiment of the method, the step of attaching the soft tissue attachment component to natural soft tissue may include fixing the natural soft tissue between the prongs of a forked end of the soft tissue attachment component. In another embodiment, attaching the soft tissue attachment component to natural soft tissue may include suturing the natural soft tissue to the soft tissue attachment component with filaments connected to the end of the soft tissue attachment component. Other embodiments may include attaching the soft tissue attachment component to a bony structure by implanting a plug into the bony structure, wherein the plug is connected to the soft tissue attachment component, or attaching the soft tissue attachment component to a bony structure by fixing a replacement or resurfacing component to the bony structure, where the replacement or resurfacing component is connected to the soft tissue attachment component.

A prosthetic humeral implant includes a stem having a coupling element at a proximal end thereof. The implant has a head having a coupling element at a distal portion thereof for coupling to the stem portion coupling element. The head has a bearing portion and a base portion. A soft tissue attachment element, having a mounting portion, extends between the bearing portion and the base portion. The soft tissue attachment portion extends proximally from the base portion. A clamp is provided for capturing the soft tissue attachment element mounting portion between the head bearing portion and base portion. The base portion may have a porous surface thereon. The porous surface may extend around a circumferential surface of the base portion. The clamp for capturing the soft tissue mounting portion may include threaded elements extending between the head bearing portion and base portion. The soft tissue attachment element may be made of a flexible material selected from the group consisting of Dacron, polytetra fluorethylene, texturized or open-weave poly(ethylene terephthalate), waterswolen poly(2-hydroxyethyl methacrylate), polydioxanone, PDO/Elastin weave, polyurethane, aromatic porous polyurethane, poly-(L-lactic acid), Polyetheratherketone, allograft or xenograft tendon or ligament, small-intestinal submucosa, collagen, cell seeded collagen matrices, hydrogels, and Chitosan. The soft tissue attachment element could also be made of metal. The humeral implant may have a tissue attachment element which has a planar surface forming the mounting portion. The humeral implant base portion may include a porous metal tissue attachment portion.

A prosthetic humeral implant includes a stem and a head coupled to the stem. The head has a base element and a bearing element slidably coupled to one another. An anti-rotation element is mounted on one of the base element and bearing element preventing rotation therebetween. A soft tissue attachment element has a first portion captured between the base element and the bearing element and a second portion extending from the base element towards the bearing element. A clamp is provided for moving the base element towards the bearing element to capture the soft tissue attachment element therebetween. The base portion may have a porous surface thereon wherein the porous surface extends around the circumference of the base portion As used herein when referring to bones or other parts of the body, the term "proximal" means close to the heart and the term "distal" means more distant from the heart. The term "inferior" means toward the feet and the term "superior" means toward the head. The term "anterior" means toward the front part or the face and the term "posterior" means toward the back of the body. The term "medial" means toward the midline of the body and the term "lateral" means away from the midline of the body.

BRIEF DESCRIPTION OF THE DRAWINGS

FIG. 1b is a lateral view of the tibial implant including soft tissue attachment device of the present invention;

FIG. 2a is a prosthetic tibia including a modular soft tissue attachment device of the present invention;

FIG. 2b is a lateral view of the tibia of FIG. 2a showing the soft tissue attachment device spaced anteriorly of the tibia;

FIG. 3b is an anterior view of the prosthetic component of FIG. 3a;

FIG. 4b is an anterior view of the prosthetic tibial component of FIG. 4a;

FIG. 4c is a lateral view of the prosthetic tibial components of FIGS. 4a and 4b;

FIG. 5a is an isometric view of yet another alternate soft tissue attachment device of the present invention showing a tibial prosthesis with a proximally extending soft tissue attachment component with resurfacing element;

FIG. 5b is a posterior view of the prosthetic tibial component of FIG. 5a;

FIG. 6a is an isometric view of yet another embodiment of the soft tissue attachment device of the present invention;

FIG. 6B is an isometric view of the embodiment of FIG. 6A with the soft tissue attachment element disassembled from the prosthetic tibia;

FIG. 7a is a front view of an additional embodiment of the present invention;

FIG. 7b is an isometric view of the ultimate embodiment of FIG. 7A with the prosthetic patellar element removed.

FIG. 10 is a view from the lateral side of the humeral implant of FIG. 8;

FIG. 11 is a cross-sectional view of the implant of FIG. 10 along the lines A-A;

FIG. 14 is a view from the lateral side of the humeral implant of FIG. 13;

FIG. 15 is an enlarged view of the humeral head shown in FIG. 13;

DETAILED DESCRIPTION

Figure 1A:
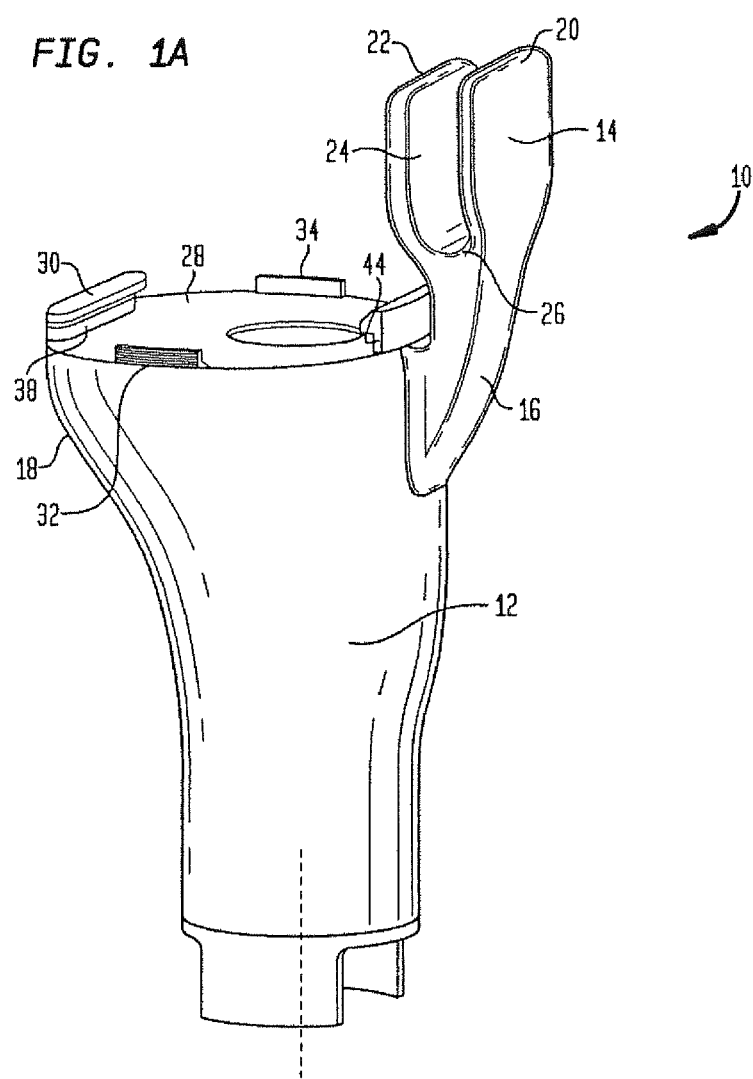
FIG. 1a is an isometric view of a prosthetic tibial implant including the soft tissue attachment device of the present invention.
Figure 1C:
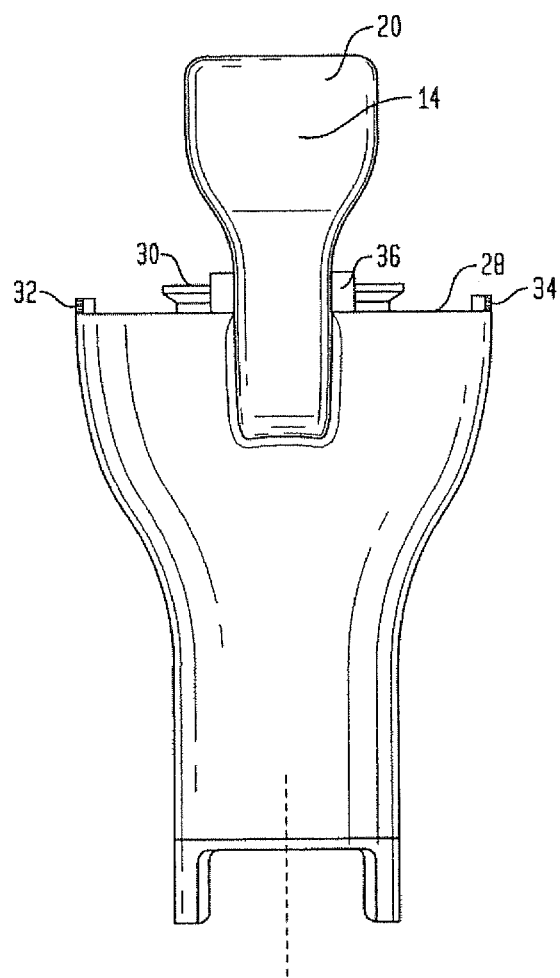
FIG. 1c is an anterior view of the prosthetic tibia shown in FIGS. 1a and 1b.
Figure 1D:
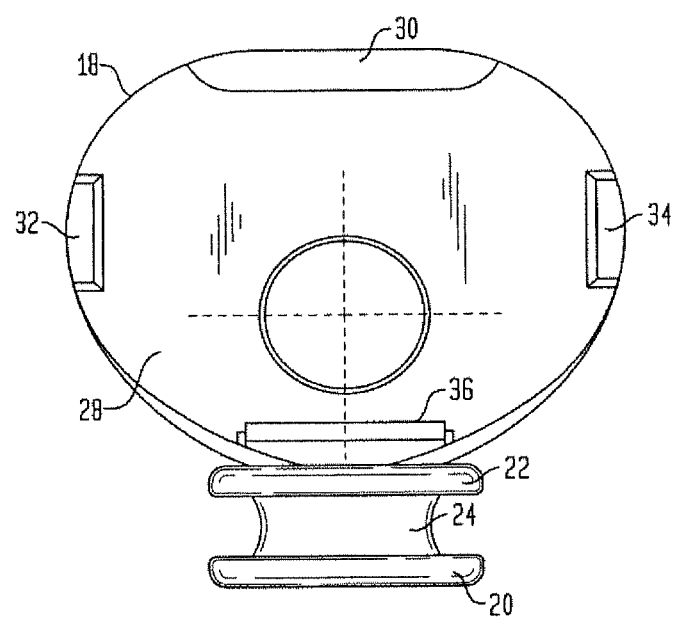
FIG. 1d is a top view of the prosthetic tibial components of FIGS. 1a through 1c showing the superior surfaces thereof.

Referring to FIGS. 1*a* through 1*d* there is shown a preferred embodiment of a prosthetic tibial component generally denoted as 10, which may be part of modular oncology system such as disclosed in U.S. Pat. No. 4,578,081. In such a system large portions of diseased bones are removed and replaced by prosthetic implants such as the proximal tibia. The tibial prosthesis includes a proximal tibial portion 12 and a proximally extending soft tissue attachment device 14. In the preferred embodiment, soft tissue attachment device 14 includes a stem portion 16, which is coupled to the proximal end 18 of prosthetic tibia 12. The device 14 may be one-piece with the proximal tibia such as by being integrally cast therewith or welded thereon. Other techniques such as Selector Laser Melting (SLM) or compression molding may also be used.

Soft tissue attachment device 14 includes first and second arms 20 and 22, which form a generally U-shaped slot 24. Slot 24 is designed to receive a portion of the patellar tendon. Arms 20 and 22 merge at a junction 26 to form stem 16. In the preferred embodiment, the proximal superior facing surface of tibial prosthesis 12 is a planar surface 28. While a U-shaped slot is shown, other shape slots may also be used.

In the preferred embodiment, surface 28 includes four proximally extending flange portions 30, 32, 34, and 36. Flange portions 30, 32, 34, and 36 are designed to receive a prosthetic bearing surface which, in the preferred embodiment, is made of ultrahigh molecular weight polyethylene (UHMWPE). However, the bearing component may be made of other polymeric or metal materials suitable for prosthetic bearings. When a UHMWPE insert (not shown) is utilized, it may be snapped and locked in recessed grooves 38, 40, 42, and 44 formed in flanges 30, 32, 34, and 36, respectively.

Referring to FIGS. 2*a* and 2*b*, there is shown a modular connection between the proximally extending tendon attachment device 14 and the proximal portion 18 of tibia prosthesis 12. The modular attachment includes a flange or plate element 40 having a pair of through holes 42 for receiving screws (not shown), which engage with threaded bores 44 and 46 in tibial prosthesis 12. Threaded bores 44 and 46 are preferably formed in a recessed area 48 formed in the anterior facing surface of the proximal tibia portion 18. The recess preferably has a distal surface 50, which receives a bottom surface 52 of flange portion 40 of the proximally extending stem portion 16 tendon attachment device 14. Surface 50 provides support for distal surface 52. As discussed above, stem portion 16 is fixedly attached to or integral with flange portion 40. The stem portion 16 may be attached by welding so that the tendon attachment device 14 is made one piece with flange portion 40.

Referring to FIG. 2*b*, flange portion 40 includes a proximally facing surface 54, which engages a distally facing surface 56 on the recessed portion 48 of prosthetic tibial component 12. Thus flange portion 40, once assembled, is prevented from proximal-distal movement by surfaces 50 and 56 of recess 48.

Figure 3A:
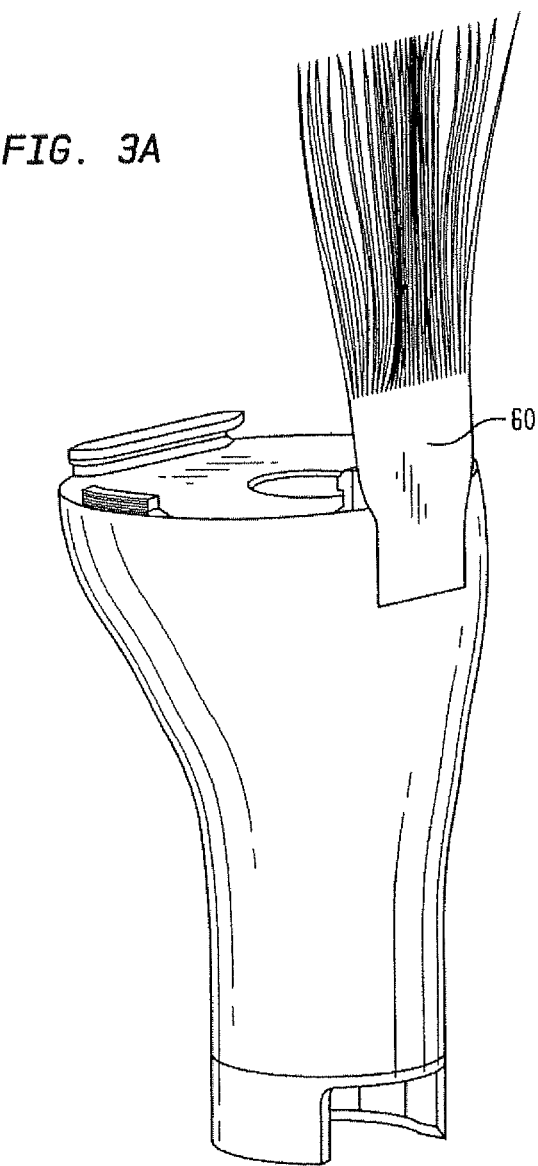
FIG. 3a is an alternate prosthetic component having a receptacle for receiving soft tissue as shown.
Figure 3B:
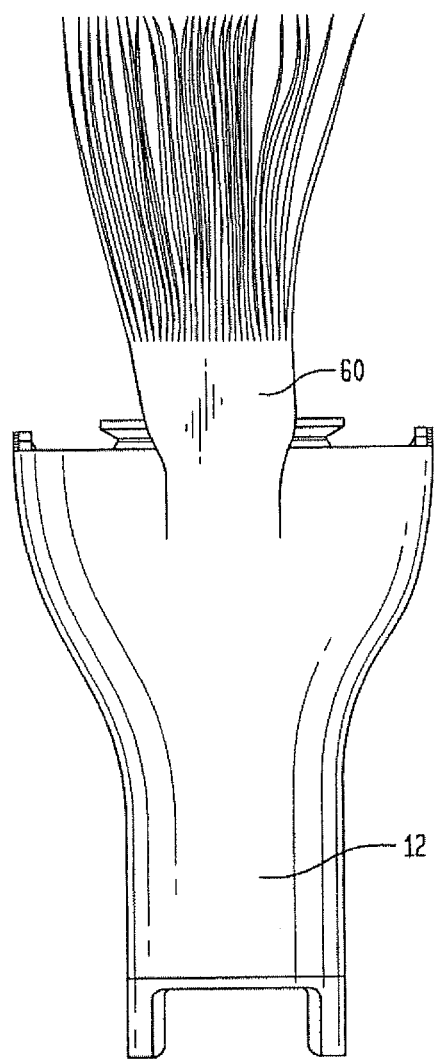
Figure 4A:
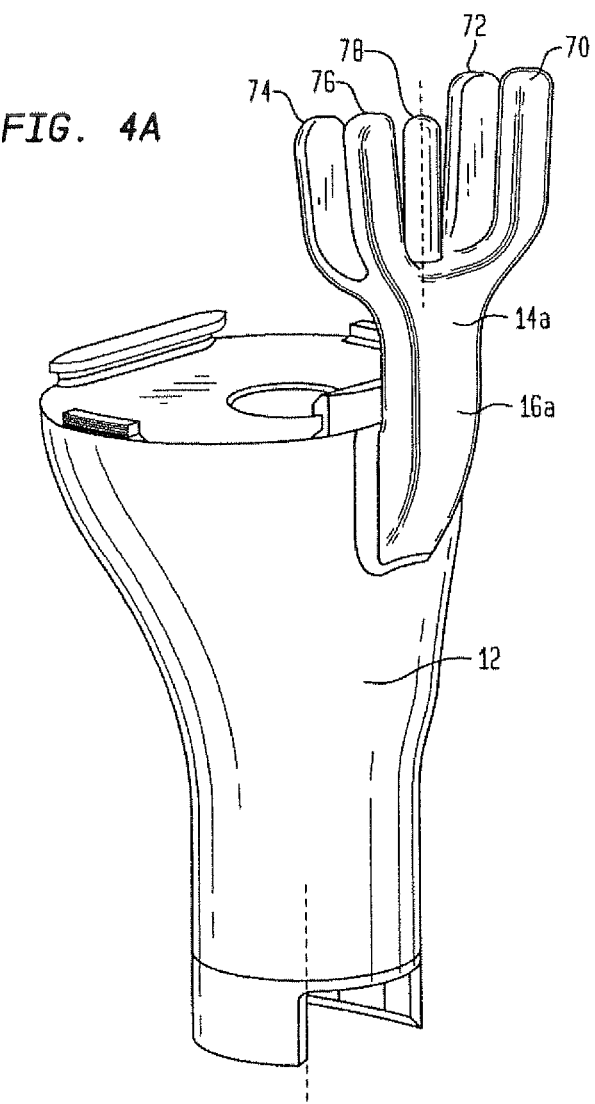
FIG. 4a is an isometric view of a prosthetic tibial implant having yet an additional alternate embodiment of the soft tissue attachment device of the present invention.
Figure 4B:
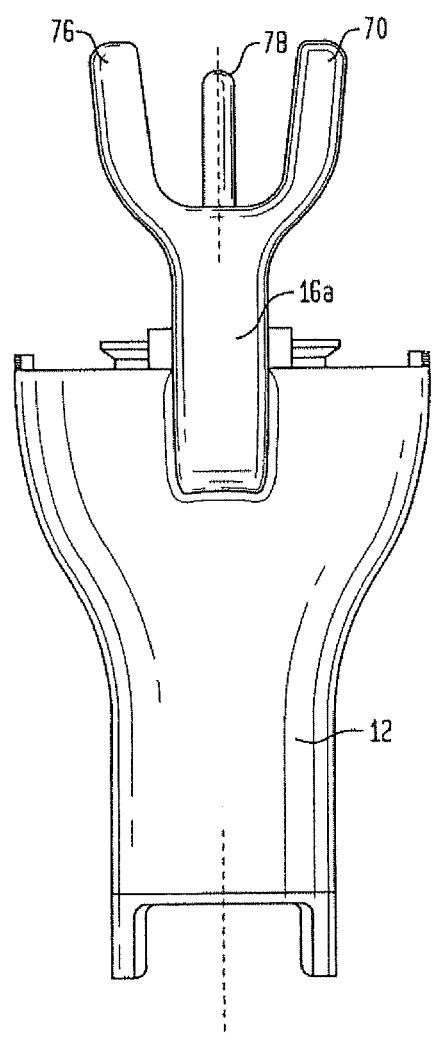
Figure 4D:
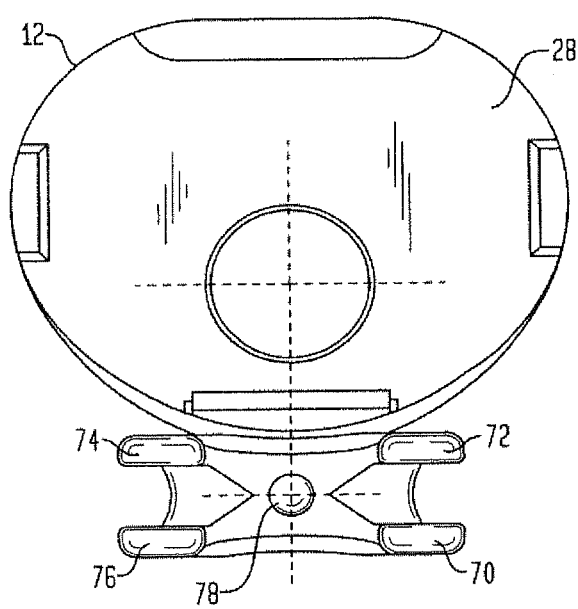
FIG. 4d is a top view of the prosthetic tibial component of FIGS. 4a through 4c joining the superior surface of the component.
Figure 5B:
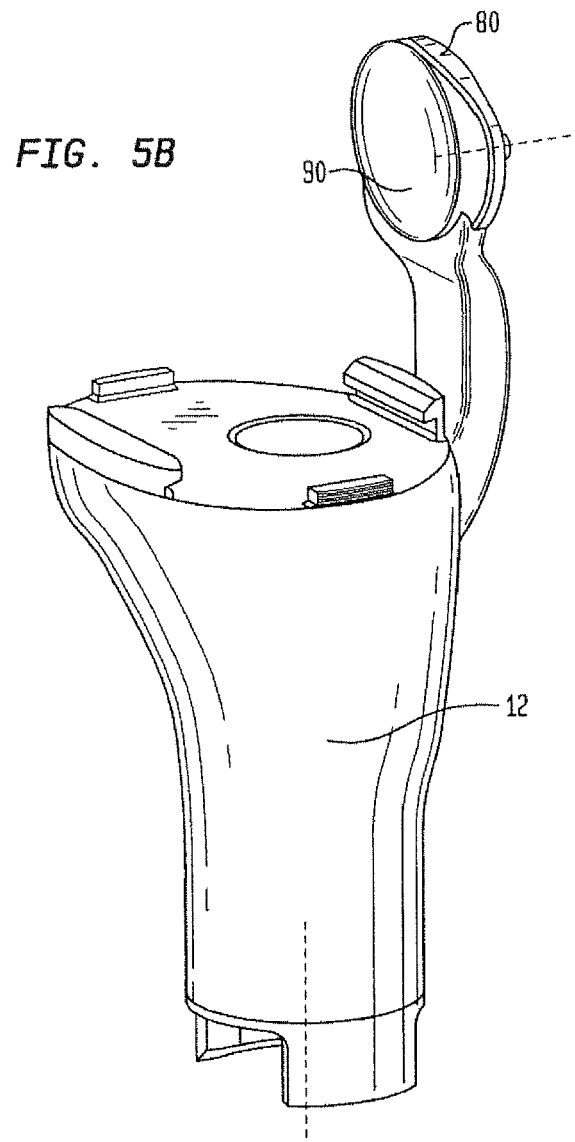
Figure 5C:
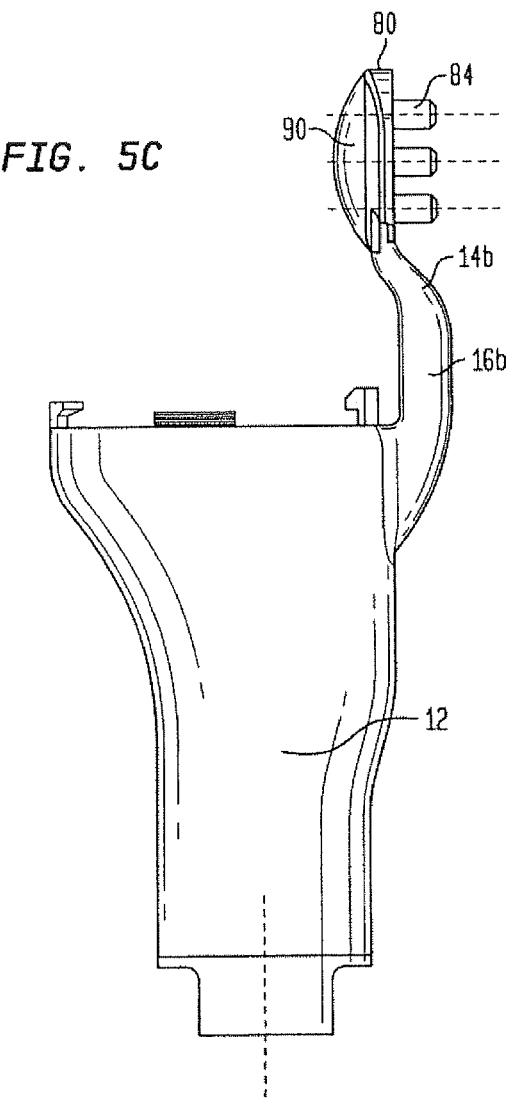
FIG. 5c is a lateral view of the prosthetic tibial component of FIGS. 5a and 5b.
Figure 5D:
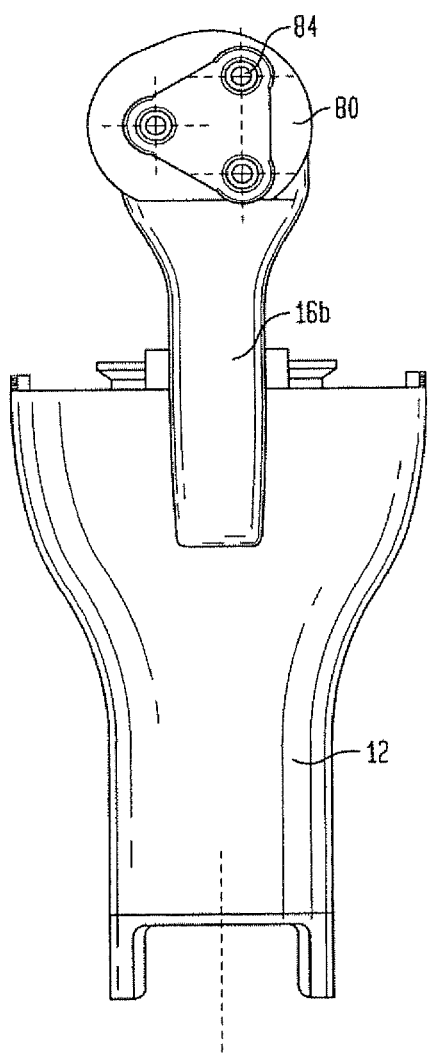
FIG. 5d is an anterior view of the soft tissue attachment device of FIGS. 5a-5c.
Figure 5E:
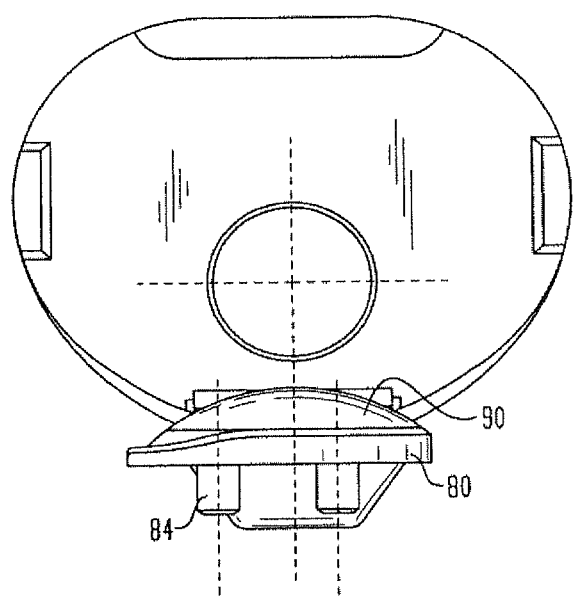
FIG. 5e is a top view of the prosthetic femoral components of FIGS. 5a-5d.

Referring to FIGS. 3*a* and 3*b*, there is shown an alternate method of attaching a tendon 60. In this embodiment the plurality of filaments are woven or stitched into soft tissue similar to suturing.

Referring to FIGS. 4*a* through 4*d*, there is shown yet an additional embodiment of the proximally extending tendon attachment device of the present invention. In this embodiment, prosthetic tibia 12 remains essentially unchanged with an alternate tendon attachment device 14*a* having a stem 16*a* attached to an anteriorly facing surface of proximal portion 18 of tibia prosthesis 12. The tendon attachment area includes four spaced arms 70, 72, 74, and 76, which form U-shaped open areas facing anteriorly and posteriorly as well as medially and laterally. A proximally facing elongate pin 78 is provided. The four spaced arms 70, 72, 74 and 76 are attached to the soft tissue in the same manner as described with respect to FIG. 1 after the plug is implanted into the patella for load sharing. Pin 78 can be cylindrical or can have other shapes.

Referring to FIGS. 5*a* through 5*e*, there is shown yet an additional design for the proximally extending tendon attachment device wherein, again the tibial prosthetic portion 12 remains the same. However, in this embodiment, a proximally extending tendon attachment device 14*b* includes a stem portion 16*b* attached to the anteriorly facing surface of the tibial prosthesis 12. A resurfacing portion 80 is provided at the proximal end of the stem 16*b*, which the resurfacing portion includes three pointed pins 82, 84, and 86. Pins 82, 84, and 86 extend anteriorly from an anterior surface 88 of resurfacing portion 80. The posterior surface of resurfacing element 80 includes a smooth portion 90, which may be part spherical in shape. Part spherical surface 90 may act as a prosthetic patellar surface once the patella is attached to pins 82, 84, and 86. In this embodiment, the stem 16*b* and attachment device 14*b* may extend anteriorly and proximally to locate surface 90 of resurfacing portion 80 at the proper location for engaging a trochlear groove of a prosthetic femoral component (not shown).

Referring to FIGS. 6*a* and 6*b* there is shown an alternate embodiment in which a soft tissue attachment element such as a patellar tendon attachment element 200 is coupled to a prosthetic tibial component 212 by clamping element 202. Attachment element 200 has a curved distal portion 204 which sits in a groove 206 formed in a recess 208 in the anterior portion of component 212. Portion 204 is clamped within recess 206 by clamp 202. Clamp 202 includes a pair of apertures 210 for receiving screws (not shown) which thread into threaded bores 214 formed in the anterior surface of component 212 in the area of recess 208. Soft tissue attachment element 200 includes an anteriorly extending portion 216 which forms a proximal part of curved distal end portion 204. Portion 216 fits within cut-out 218 of clamp 202 when the soft tissue attachment element 200 is assembled as shown in FIG. 6A.

Figure 7C:
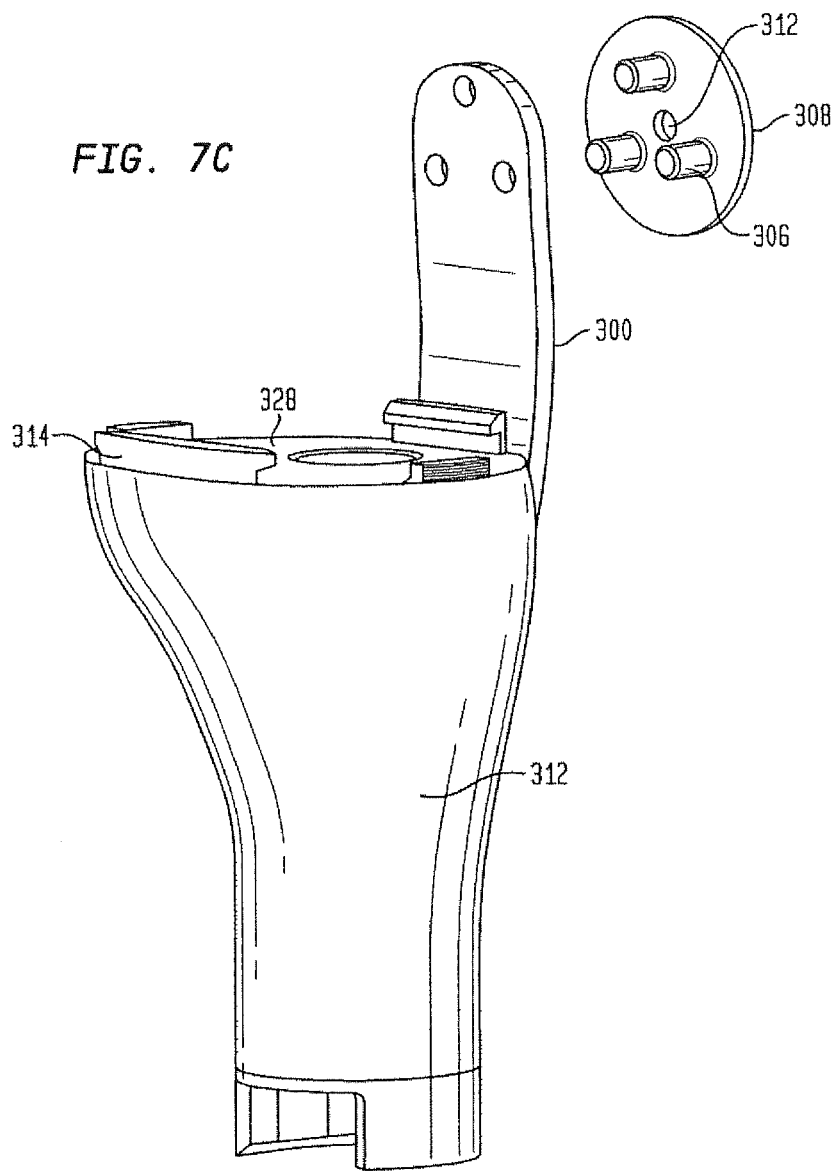
FIG. 7c is a posterior view of the embodiment of FIGS. 7a and 7b with the prosthetic patella disassembled from the soft tissue attachment device.

Referring to FIGS. 7a-7c, a proximal tibial component 312 with an integral soft tissue attachment element 300 integrally formed therewith such as by welding or casting. Soft tissue attachment element 300 includes a proximal end 302 having a plurality of through holes 304 for receiving the pegged posterior receiving peg elements 306 of a prosthetic patellar component 308. A small protrusion 310 is formed on the anterior face of proximal end 302 of soft tissue attachment element 300. Protrusion 310 extends into a recessed bore 312 formed on the posterior face of prosthetic patella 308. As in all of the other embodiments the proximal surface 328 includes locking elements 314 for fixing a ultra high molecular weight polyethylene bearing surface to the proximal tibia. Such structures are well known in the art.

Figure 8:
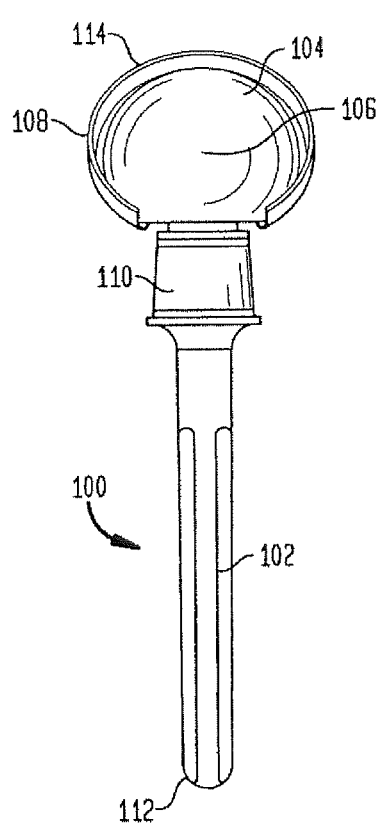
FIG. 8 is a view of the medially facing side of the humeral implant with soft tissue attachment device of the present invention.
Figure 9:
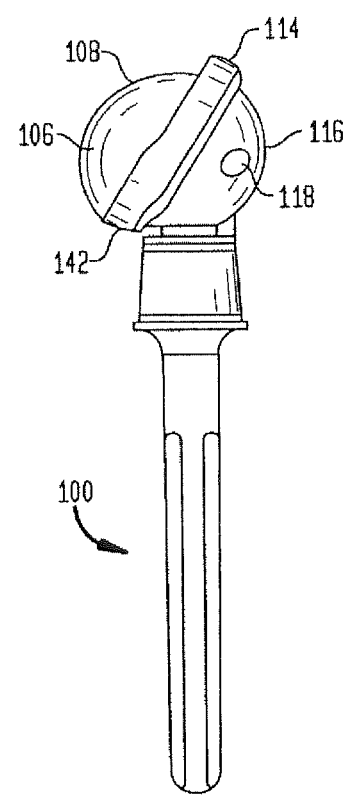
FIG. 9 is an anterior or posterior view of the humeral implant of FIG. 8.

Referring to FIG. 8 there is shown a humeral implant assembly generally designated as 100 viewed medially from the center of the body. The implant 100 has a distal item 102 and a proximal end 104. Proximal end 104 includes a typical bearing surface 106 which engages a glenoid component (not shown) when used in a total shoulder replacement. In one embodiment the bearing surface 106 is mounted on a modular proximal head element 108 which is connected via a body element 110 to distal stem portion 102. Stem portion 102 has a tip 112 which is adapted to be inserted into the intramedullary canal of the proximal humerus such that stem 102 is located within the canal. Stem 102 may be of any standard design. Preferably body portion 110 includes a conically tapered male trunion for placement in a conically tapered female receptacle on head 108. This coupling system can be seen, for example, in FIG. 11. The tapered system can use a standard Morse type taper connection or any acceptable connection mechanism. Attached to head 108 is a tissue attachment element 114 which extends medially and proximally towards the glenoid when the humeral implant 100 is implanted within the humerus. Referring to FIG. 9, there is shown humeral implant 100 when viewed either anteriorly or posteriorly. As can be seen bearing surface 106 is oriented to engage a prosthetic glenoid (not shown) and tissue attachment element 114 is oriented to allow attachment of soft tissue such as ligaments and tendons of the shoulder. As discussed herein below, a laterally facing surface 116 of head portion 108 includes a bore 118 for receiving a clamping screw 118 best seen in FIG. 12. As shown in FIG. 10 a similar screw 118 is located on the opposite anterior or posterior side of implant 100. While the humeral implant 100 is described as a modular implant having separate head and stem portions, these portions could easily be combined into a one-piece design without departing from the spirit and scope of this invention.

Referring to FIG. 10, there is shown humeral implant 100 when viewed from laterally of the body. As such surface 116 can be viewed along with the two screw containing bores 118. It can be seen that tissue attachment element 114 extends circumferentially around head portion 108 with the exception of the distal-most portion 119 of the head 108. Distal gap 119 of tissue attachment element 114 prevents its contact with bony anatomic structures.

Figure 12:
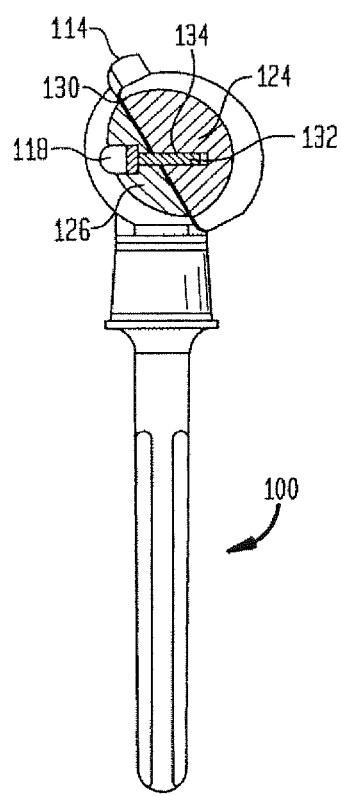
FIG. 12 is a cross-sectional view of the implant of FIG. 10 along lines B-B.

Referring to FIG. 11, there is a cross-sectional view of the implant of FIG. 10 along lines A-A. As can be seen, the proximal end of body portion 110 includes a conically tapered trunion 120 which is received within a conically tapered receptacle 122 in the head portion 108. Head portion 108 is preferably made in two parts. First part 124 includes bearing surface 106 and a second part 126 includes trunion receiving bore 122. A clamping interface 128 extends circumferentially around a junction between first part 124 and second part 126. Parts 124 and 126 have matching planar circumferential surfaces which may clamp together. Of course any clamping system may be utilized. Interface 128 receives a mounting portion or flange 130 of soft tissue attachment element 114 as best seen in FIG. 12. Portion 130 is connected to a flange portion 131 of tissue attachment element 114.

Referring to FIG. 12 there is shown a cross-section of the prosthetic implant of FIG. 10 along the lines B-B showing bore 118 housing a screw 132. As can be seen in FIG. 10, there are two screws 132 located on the anterior and posterior sides of the implant. The tightening of screw 132 into threaded bore 134 of part 124 clamps portion 130 of tissue attachment element 114 in position. While threaded screws are shown, any other method of attaching element 114 to head 108 may be utilized. For example, other clamping, pin, tabs, welding, press-fit, quick-connect or taper lock.

Regarding soft tissue attachment element 114, this element may be made of a material such as Dacron, polytetra fluorethylene, texturized or open-weave poly(ethylene terephthalate), waterswollen poly(2-hydroxyethyl methacrylate), polydioxanone, PDO/Elastin weave), polyurethane, aromatic porous polyurethane, poly-(L-lactic acid), Polyetheratherketone, allograft or xenograft tendon or ligament, small intestinal submucosa, collagen, cell seeded collagen matrices, hydrogels and Chitosan.

Figure 13:
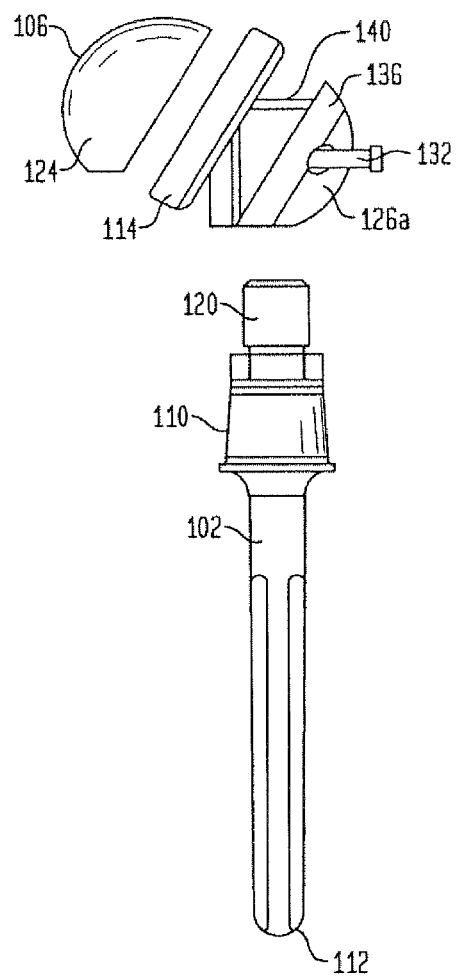
FIG. 13 is an exploded view of the humeral implant of FIG. 8.

Referring to FIG. 13, there is shown the prosthetic humeral implant of FIGS. 8-12 with all the parts disassembled. Stem 102 and body 110 including trunion 120 are, in the preferred embodiment, monolithic, although these parts can be modularized in a well known fashion with additional male and female tapered interconnections similar to the morse type taper of trunion 120. Head portion 108 is shown disassembled into first element 124 which includes articular surface 106 and second section 126 which includes screw 132 extending into bore 118. Portion 131 of tissue attachment element 114 is shown extending partially circumferentially around the interface 128 between sections 124 and 126. In the embodiment shown in FIGS. 13-15, a porous tissue attachment surface 136 is shown formed on an outer circumference of second section 126 of head 108. Porous tissue attachment portion 136 may be a porous titanium metal, foam metal, porous surface produced by selective laser melting or may be a roughened surface. Any structure that provides a conductive structure to allow the natural tissue of the patient to adhere or to ingrow over time following implantation can be used. These surfaces may be coated with a biological treatment such as a bone morphogenic protein solution or be coated with hydroxapatite to enhance or promote biologic attachment or incorporation of the shoulder joint tissue onto the implant. A bone morphogenic protein that may be utilized is OP-1 sold by Stryker Corporation.

Referring to FIG. 15 there is an alternate embodiment of head 108 which is the same in all respects except that first section 124a includes a porous tissue ingrowth surface 138, which, upon assembly, is located adjacent porous surface 136. Porous surfaces 136 and 138 may be identical structures as discussed above with respect to surface 136.

Figure 16:
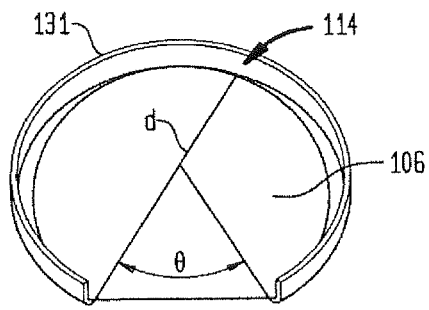
FIG. 16 is a view of the medial side of the head portion of the humeral implant of FIG. 8 showing the bearing surface and tissue attachment elements.
Figure 17:
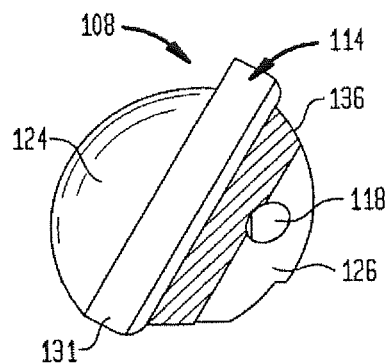
FIG. 17 shows the humeral head of the humeral implant of FIG. 13 in an assembled position.
Figure 18:
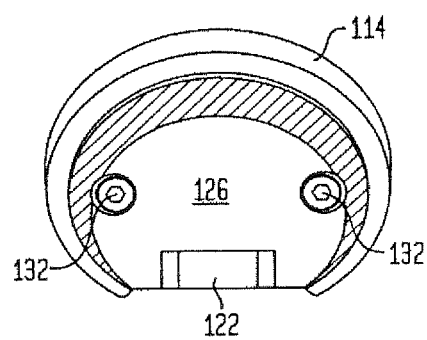
FIG. 18 is a lateral view of the humeral head of FIG. 17.

As can be seen in FIGS. 13 and 15 second section 126 of head 108 preferably has a smooth part spherical laterally facing surface and a part rectangular medially facing protruding portion 140. The laterally facing surface of first portions 124 and 124a include a rectangular recess for receiving protruding portion 140 which recesses include a pair of threaded bores 134 extending therefrom into portions 124, 124a. The rectangular mating structure is a matter of design choice and any mating structure which prevents rotation of first portion 124, 124a with respect to second portion 126, 126a could be utilized. Referring to FIGS. 16-18, head 108, including second section 126a, with tissue ingrowth portion 136, is shown in an assembled condition. FIG. 16 shows a view from the medial part of the body including medially and proximally extending flange portion 131 of tissue attachment element 114 which extends approximately 290° circumferentially making the angle θ approximately 70°. In a typical embodiment, the diameter d of the tissue attachment element is approximately two inches with the head 104 having a proximal distal dimension of about 1.5 inches and a medial-lateral width of approximately 1.6 inches. These dimensions of course may change depending on the implant size. In addition, the length of a tissue attachment flange portion 131 of tissue attachment element 114 may be between approximately 0.35 and 0.8 inches. This distance can be made longer if the surgeon prefers.

Figure 19:
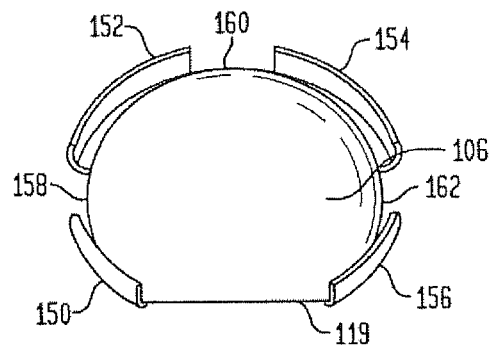
FIG. 19 is a view similar to FIG. 16 showing an alternate tissue attachment element.
Figure 20:
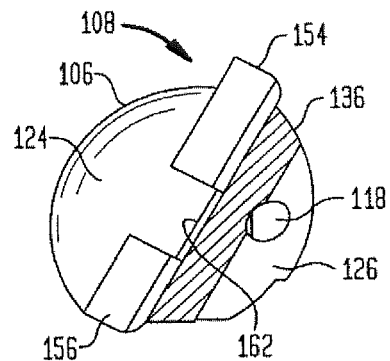
FIG. 20 is an anterior/posterior view of the humeral head of FIG. 19.
Figure 21:
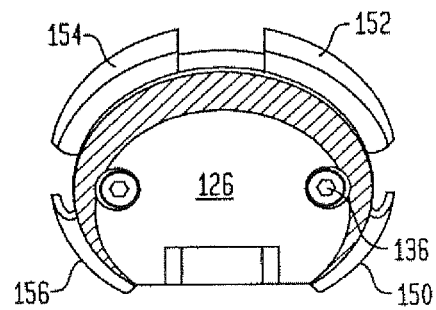
FIG. 21 is a lateral view of the humeral head embodiment of FIG. 20.

Referring to FIGS. 19-21 there is shown an alternate embodiment of the head 108 shown in FIGS. 16-18. In the alternate embodiment of FIGS. 19-21, the tissue attachment element 114 is interrupted and, in the embodiment shown, includes four segments 150, 152, 154 and 156. The segments 150, 152, 154 and 156 form three interruptions 158, 160 and 162. These interruptions may be located at any angle and at any desired length. For that matter only a single interruption in addition to gap 119 can be used. The purpose of the interruptions are to have the ability to attach muscles/tendons in specific locations.

Figure 22:
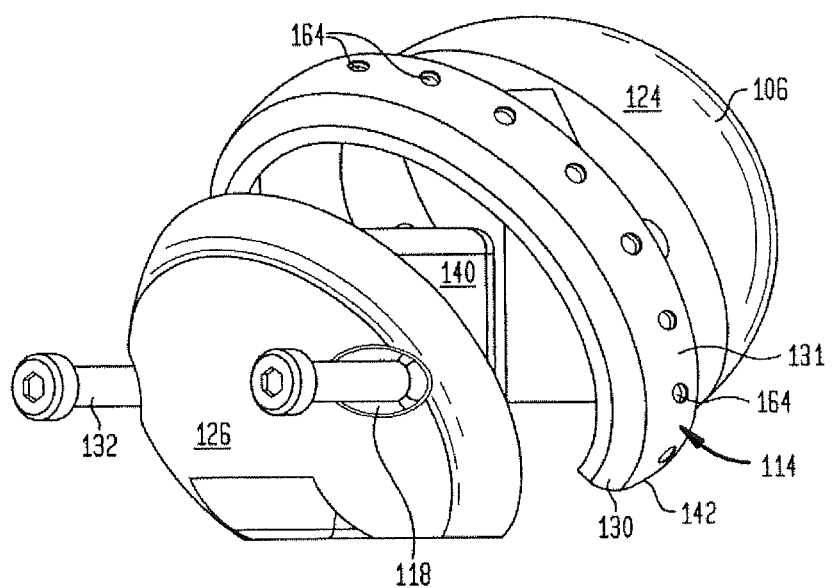
FIG. 22 is an exploded view of an alternate embodiment of a humeral head including a tissue attachment element having suture attachment openings.

Referring to FIG. 22, there is shown an alternate embodiment in which flange 131 of soft tissue attachment element 114 includes a plurality of suture through holes 164. The through holes 164 may be spaced evenly around the circumference of tissue attachment element 114 and are adapted to allow sutures extending through soft tissue to be attached to flange portion 131 of element 114.

Figure 23:
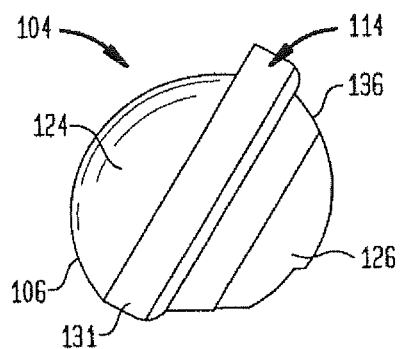
FIG. 23 shows a humeral head having a tissue attachment portion on a lateral surface thereof.
Figure 24:
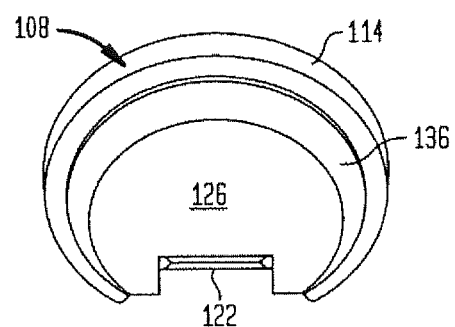
FIG. 24 is a lateral view of the assembled head component of FIG. 23.

Referring to FIGS. 23 and 24, there is shown an alternate embodiment of humeral head 108 in which the elements are manufactured in one piece. In this embodiment, the soft tissue attachment element 114 has been captured within head 108 by a manufacturing process such as injection or compression molding. In this method the soft tissue attachment element is positioned in the mold and the implant material is compressed onto it to capture it in the head. As described previously, this embodiment may also have porous metal region 136.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A prosthetic bone implant, the bone implant forming one side of a joint, comprising:
a prosthesis;
a soft tissue attachment component connected to the bone implant and extending outwardly therefrom and towards a joint line and extends beyond the joint line;
wherein the soft tissue attachment component is moveable with respect to the prosthesis while connected thereto; and
wherein the soft tissue attachment component has a first end and a second end, the first end configured to connect to the prosthesis and the second end including a forked tip configured to engage a soft tissue, the connection between the first end of the tissue attachment component and the prosthesis allowing the connection to occur after implantation of the prosthetic bone implant.

2. The prosthetic bone implant of claim 1, wherein the soft tissue attachment component has a first end and a second end, the first end configured to attach to the prosthesis and the second end including a plug configured for attachment to bone.

3. The prosthetic bone implant of claim 1, wherein the soft tissue attachment component has a first end and a second end, the first end configured to attach to the prosthesis and the second end attached to a replacement or resurfacing element for a bony structure.

4. The prosthetic bone implant as set forth in claim 1 wherein the first end includes a stem portion which is coupled to the prosthesis.

5. The prosthetic bone implant as set forth in claim 4 wherein the stem portion is fixedly held on the prosthesis by screws.

6. The prosthetic bone implant as set forth in claim 4 wherein the stem portion includes a flange and the prosthesis includes a recess for receiving the flange.

7. The prosthetic bone implant as set forth in claim 6 wherein the flange has a surface facing the soft tissue attachment component second end engaging a stop surface in the recess.

8. The prosthetic bone implant of claim 1, wherein the soft tissue attachment component is at least partially porous.

9. The prosthetic bone implant of claim 1, wherein the soft tissue attachment component has a variable porosity throughout its length or throughout its cross section, or throughout both its length and its cross section.

10. A prosthetic bone implant, the bone implant forming one side of a joint, comprising:
a prosthesis for replacing one side of a joint, the prosthesis having a bearing surface located on one side of a joint line; and
a soft tissue attachment component having a flange portion fixedly connected to the prosthesis adjacent at a first end and extending outwardly therefrom beyond the joint line at a second end, the soft tissue attachment component further comprises a stem portion formed as a one-piece construct with the flange portion, the stem portion having a free end with first and second arms forming a U-shaped slot, the U-shaped slot being open proximally at a free end thereof and having two medial and lateral side openings extending from the open free end of the slot distally towards the stem portion the flange portion has a plurality of holes therethrough and the prosthesis has a recessed area with threaded bores aligned with the holes in the flange and the flange is held on the prosthesis with screws;
wherein the soft tissue attachment component is moveable with respect to the prosthesis while connected thereto.

11. The prosthetic bone implant of claim 10, wherein the soft tissue attachment component is at least partially porous.

12. The prosthetic bone implant of claim 10, wherein the soft tissue attachment component has a variable porosity throughout its length or throughout its cross section, or throughout both its length and its cross section.

13. The prosthetic bone implant of claim 12 wherein the soft tissue attachment component is formed integrally with the replacement or resurfacing element.

14. The prosthetic bone implant of claim 10 wherein the prosthesis and the soft tissue attachment mechanism are configured to be connected at the time of surgery.

15. The prosthetic bone implant of claim 10, wherein the soft tissue attachment component is configured to be modified by a surgeon according to the size and tension needs of a particular procedure.

16. The prosthetic bone implant of claim 10, wherein the soft tissue attachment component is composed at least in part of a material that is either synthetic or biologic, or a composite of synthetic and biologic materials.

17. A prosthetic bone implant, the bone implant forming one side of a joint, comprising:
   a prosthesis;
   a soft tissue attachment component connected to the bone implant and extending outwardly therefrom and towards a joint line and extends beyond the joint line;
   wherein the soft tissue attachment component is moveable with respect to the prosthesis while connected thereto;
   wherein the soft tissue attachment component has a first end and a second end, the first end configured to attach to the prosthesis and the second end including a forked tip configured to engage a soft tissue wherein the first end includes a stem portion which is coupled to the prosthesis; and
   wherein the stem portion includes a flange and the prosthesis includes a recess for receiving the flange.

18. The prosthetic bone implant as set forth in claim 17 wherein the flange has a surface facing the soft tissue attachment component second end engaging a stop surface in the recess.

19. The prosthetic bone implant as set forth in claim 17 wherein the stem portion is fixedly held on the prosthesis by screws.

* * * * *